United States Patent [19]

Alving et al.

[11] Patent Number: 6,093,406
[45] Date of Patent: Jul. 25, 2000

[54] VACCINE FOR INDUCTION OF IMMUNITY TO MALARIA

[75] Inventors: Carl R. Alving, Bethesda; Roberta R. Owens, Silver Springs, both of Md.

[73] Assignee: The United States of America as represented by the Secretary of the Army, Washington, D.C.

[21] Appl. No.: 08/396,281

[22] Filed: Feb. 27, 1995

Related U.S. Application Data

[63] Continuation of application No. 07/796,279, Nov. 22, 1991, abandoned, which is a continuation of application No. 07/202,509, Jun. 2, 1988, abandoned.

[51] Int. Cl.[7] ...................... A61K 39/015; A61K 39/127; A61K 39/02; A61K 39/00
[52] U.S. Cl. .................................... 424/272.1; 424/184.1; 424/234.1; 424/265.1; 424/278.1; 424/282.1; 424/283.1; 424/400; 424/417; 424/420; 424/450; 424/268.1
[58] Field of Search ............................... 424/268.1, 278.1, 424/282.1, 283.1, 420, 184.1, 234.1, 265.1, 272.1, 400, 417, 450

[56] References Cited

U.S. PATENT DOCUMENTS

| | | | |
|---|---|---|---|
| 4,416,872 | 11/1983 | Alving et al. | 424/177 |
| 4,847,080 | 7/1989 | Neurath et al. | 424/89 |
| 4,877,611 | 10/1989 | Cantrell | 424/88 |
| 5,026,557 | 6/1991 | Estis | 424/450 |

FOREIGN PATENT DOCUMENTS

| | | | |
|---|---|---|---|
| 0192626 | 8/1996 | European Pat. Off. | C12N 15/00 |
| 8706939 | 11/1987 | WIPO | C07K 3/18 |

OTHER PUBLICATIONS

Edelman. Reviews of Infectious Diseases 2(3):370–383, 1980.
Alving. Liposomes As Carriers for Vaccines. In: Diposomes: From Biophysics To Therapeutics Marcel Dekker, New York, 1987. pp. 195–218.
Lehninger (Principles of Biochemistry, Worth Publishers Inc, New.
Gregoriadis et al, Drugs 45(1): 15–28, 1993.
Brown et al, Vaccine 12(2):102–108, 1994.
Berzofsky et al, Immunological Reviews 98:9–52, 1987.
Davis Jr. Vaccine 12(47):321–328, 1994.
Ballov et al, Lancet I 1277–1282, 1987.
Butcher GA. Parisitology 98:315–327, 1989.
Leningher AL *Principles of Biochemisrty*, Worth Publishers, Inc. (N.Y.), 1982 pp. 310–311.
Alving et al, Vaccine, vol. 4, pp. 166–172, (Sep. 1986).
Richards et al, Infection and Immunity, vol. 56, pp. 682–686, (Mar. 1988).
Patammogo et al, Nature, vol. 328, pp. 629–632, (Aug. 1987).

*Primary Examiner*—James C. Housel
*Assistant Examiner*—V. Ryan
*Attorney, Agent, or Firm*—Elizabeth Arwine; Charles H. Harris; John Francis Moran

[57] ABSTRACT

Vaccines for the induction of immunity to malaria, based on aluminum hydroxide-treated, lipid A- and malarial antigen-containing liposomes, are described. Vaccines of this sort are useful in both humans and animals.

22 Claims, 6 Drawing Sheets

VACCINE FOR INDUCTION OF IMMUNITY
TO MALARIA

This application is a continuation of application Ser. No. 07/796,279, filed Nov. 22, 1991 now abandoned, which is a continuation of Ser. No. 07/202,509 filed Jun. 2, 1988 now abandoned.

BACKGROUND OF THE INVENTION

The present invention relates to a vaccine that comprises liposomes adsorbed to aluminum hydroxide, the liposomes comprising lipid A and a molecule ("malarial antigen") that is capable of inducing an immune response against a malarial parasite in man or in an animal species. The present invention also pertains to a method of inducing an immune response in a mammal against a malarial parasite by injection of the above-described vaccine.

In the normal course of malarial infection, the parasitic malarial organism, in the form of a sporozoite, is transmitted to an animal host by the bite of a mosquito. Shortly thereafter, the sporozoite invades the host's liver where it replicates and produces numerous merozoites. These merozoites then invade the erythrocytes of the host.

In the development of a vaccine for protection of man and animals against malaria, therefore, it is desirable to produce a vaccine that can induce immunity against one of the life forms of the malarial parasite. For example, a vaccine can be developed against the sporozoites and thereby prevent invasion of the liver tissue and replication of the parasite. But in order for the induced immune response to be effective, the anti-sporozoite antibody titer must be sufficiently high (1) to maintain protective activity over a long period of time, preferably more than a year, and (2) to block sporozoite invasion of the liver within the short period of time after infection and before invasion of the liver.

Sporozoites are known to possess an antigenic surface protein known as a circumsporozoite ("CS") protein. The gene encoding the CS protein from *Plasmodium falciparum* has been cloned, and the amino acid sequence of this CS protein has been determined. It has been found that the middle portion of the CS protein comprises a region that has thirty-seven Asn-Ala-Asn-Pro tetrapeptides interspersed with four Asn-Val-Asp-Pro tetrapeptides. Peptides comprising various multiples of at least one of these two tetrapeptides are herein collectively referred to as "CS peptides."

Young et al, Science 228: 958–962 (1985), found that the highest antibody titer that could be induced in mice against the malarial parasite occurred when these animals were injected with CS peptides in admixture with complete Freund's adjuvant ("CFA"). When the mice were immunized with CS peptides adsorbed to aluminum hydroxide, without CFA, an intermediate level of antibody titer was obtained. Injection of one CS peptide, R16tet$_{32}$, alone into mice induced very little immune response. It appears, therefore, that CRA is capable of enhancing the immune response of mice to a non-immunogenic CS peptide.

In the present description, "R16tet$_{32}$" denotes a synthetic peptide that has (1) fifteen Asn-Ala-Asn-Pro tetrapeptide repeats and one Asn-Val-Asp-Pro tetrapeptide and (2) thirty-two amino acids derived from a tetracycline resistance gene. In like fashion, "R32tet$_{32}$" and "R48tet$_{32}$" denote peptides that are similar to R16tet$_{32}$ but that have two and three copies, respectively, of the sixteen tetrapeptides of R16tet$_{32}$.

For purposes of vaccination in human, use of CFA is not desirable because of its severe side effects. Therefore, alternative adjuvants for stimulating the immunogenicity of antigens for use in man are sought. Liposomes have been used as an alternative adjuvant in animal systems. The ability of different liposomes to enhance immune response, however, has been variable.

For example, Allison and Gregoriadis, Nature 252: 252 (1974), reported that the use of negatively charged or neutral liposomes effectively induced a higher immune response to diphtheria toxoid ("DT") in mice, but that use of positively charged liposomes led to a weaker immune response than was obtained with the use of DT alone. In other studies in which other antigens were used, positively charged and negatively charged liposomes were found to be equally effective as adjuvants. See Heath et al., Biochem. Soc. Trans. 4: 129–133 (1976), and van Rooijen and van Nieuwmegen, Immunol. Commun. 9: 243–256 (1980). Accordingly it appears that whether liposomes can act as adjuvant varies from antigen to antigen.

Alving et al., Vaccine 4: 166–172 (1986) used liposomes comprising lipid A as adjuvants in inducing immunity in rabbits to cholera toxin ("CT") and to a synthetic CS peptide consisting of four Asn-Pro-Asn-Ala tetrapeptides conjugated to BSA. The authors found that the immune response to CT or to the synthetic malaria peptide was markedly enhanced by use of liposomes and lipid A, compared to similar liposomes lacking lipid A.

In contrast, Gerlier et al., J. Immunol. 131: 485–490 (1983), found in rats that liposomes comprising the same lipid A as used by Alving and his coworkers did not stimulate a greater immune response to antigens derived from cells infected with Gross virus. Hence, it again appears that the ability of liposomes with lipid A alone to serve effectively as adjuvants varies depending on the antigen and, perhaps, on the animal system used.

SUMMARY OF THE INVENTION

It is an object of the present invention, therefore, to provide a vaccine suitable for induction of immunity against malaria in man and/or animals.

It is also an object of the present invention to provide a vaccine comprising an adjuvant that is capable of enhancing the immune response to a malarial antigen in man and/or in animals.

It is another object of the present invention to provide a vaccine to a malarial antigen that does not require the use of a large quantity of such an antigen.

It is a further object of the present invention to provide a method for inducing immunity in humans or animals to a malarial parasite by use of a vaccine as described above.

In accomplishing these and other objects, there has been provided a vaccine comprising liposomes adsorbed to aluminum hydroxide, wherein said liposomes comprise lipid A and a malarial antigen.

In accordance with a further aspect of the present invention, there has been provided a method of inducing an immune response against a malarial parasite comprising the step of injecting a mammal with a vaccine as described above.

Further objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

Each of (a), (b) or (c) above is injected intramuscularly into a group of 4 monkeys at 0 and 4 weeks. Each dose comprises 40 μg of R32tet$_{32}$ in a volume of 0.5 ml. The immune response is expressed as units of ELISA activity or absorbance at 414 mn. Each data point represents the mean response of 4 monkeys injected in the manner indicated. The serum dilution employed was 1:400 dilution.

Figure 1:
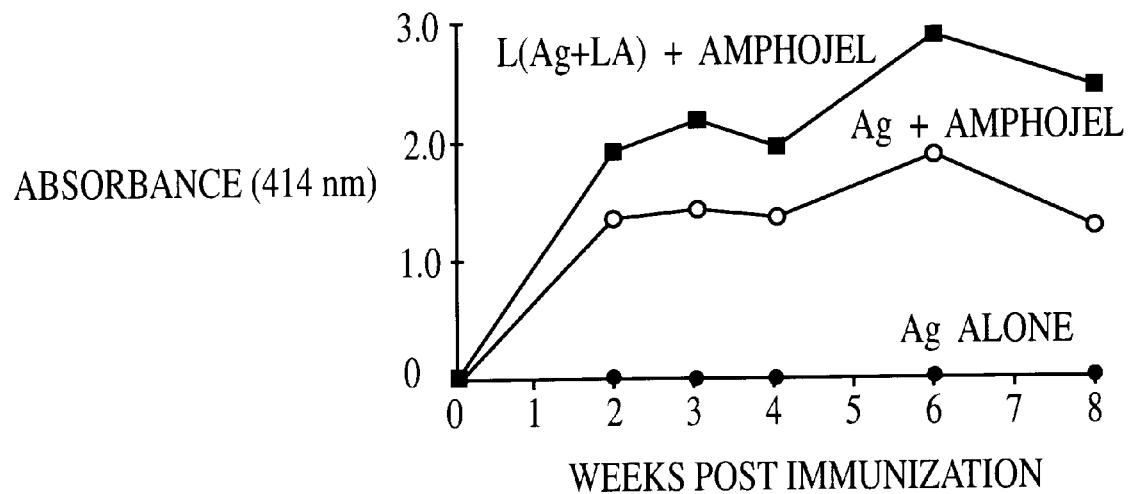
FIG. 1 shows the immune response in Rhesus monkeys as a function of time after injection of (a) R32tet$_{32}$ ("Ag alone"), (b) R32tet$_{32}$ adsorbed to Amphojel® ("Ag+Amphojel") or (c) liposomes that comprises R32tet$_3$2 and lipid A, and that are adsorbed to Amphojel® ["L(Ag+LA)+Amphojel"].
Figure 2:
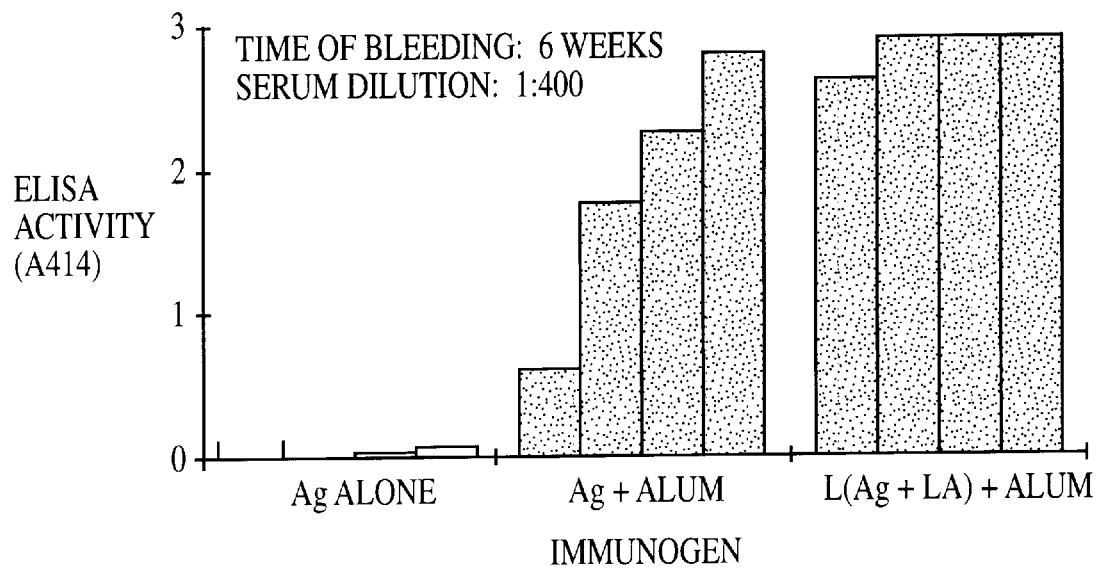

FIG. 2 shows the immune response of individual monkeys immunized as described under FIG. 1 above at 6 weeks after primary immunization.

Figure 3:
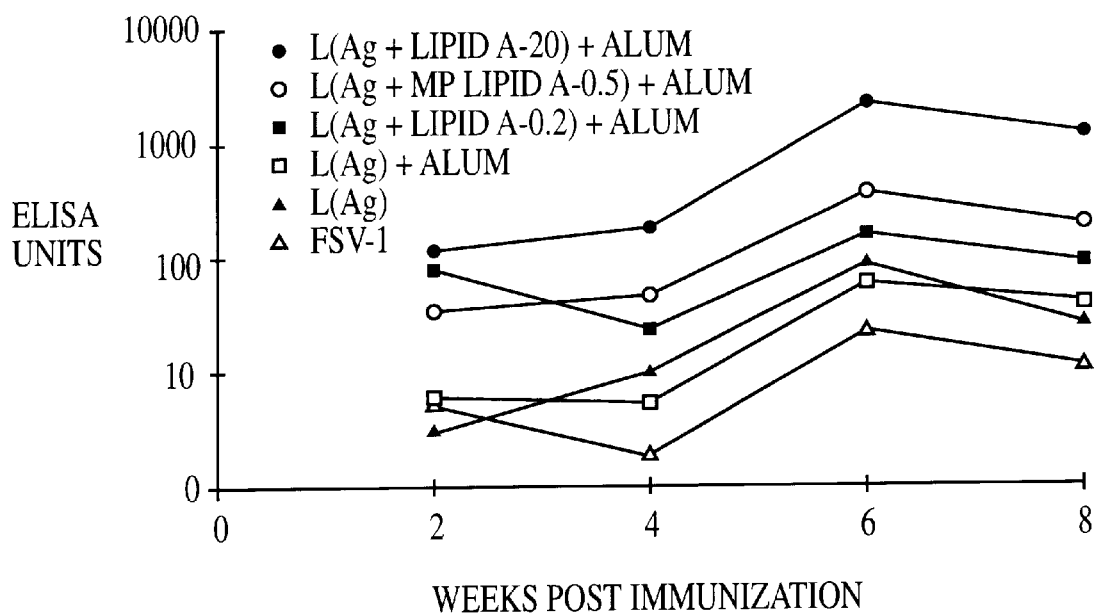

FIG. 3 shows the time course of the immune response to liposomal vaccines in monkeys expressed as ELISA units. Each point represents the average ELISA units for 4 monkeys after subtraction of the prebleed values.

Figure 4:
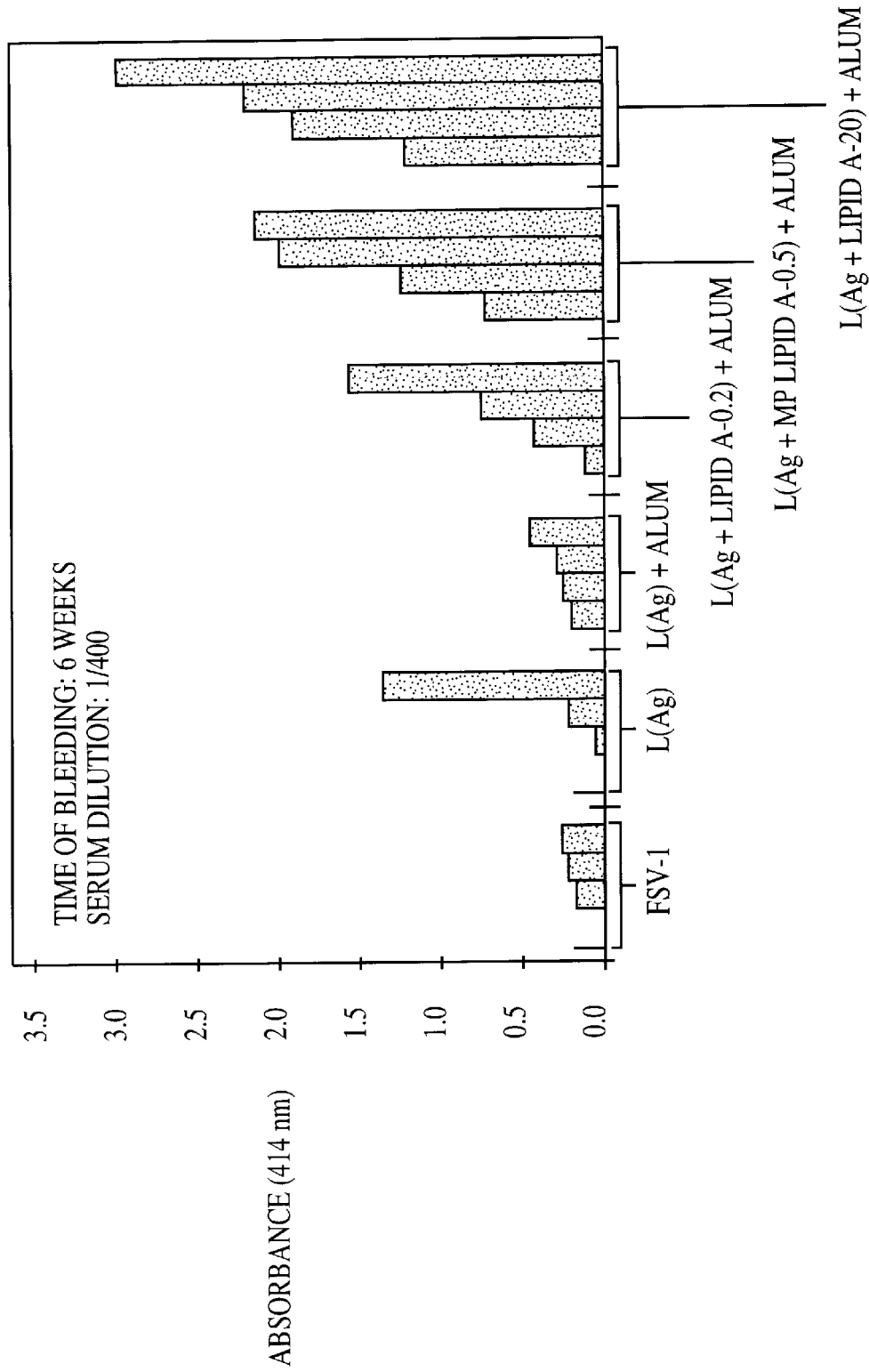

FIG. 4 shows the immune response of individual monkeys to liposomal R32tet$_{32}$ at 6 weeks after primary immunization.

Figure 5:
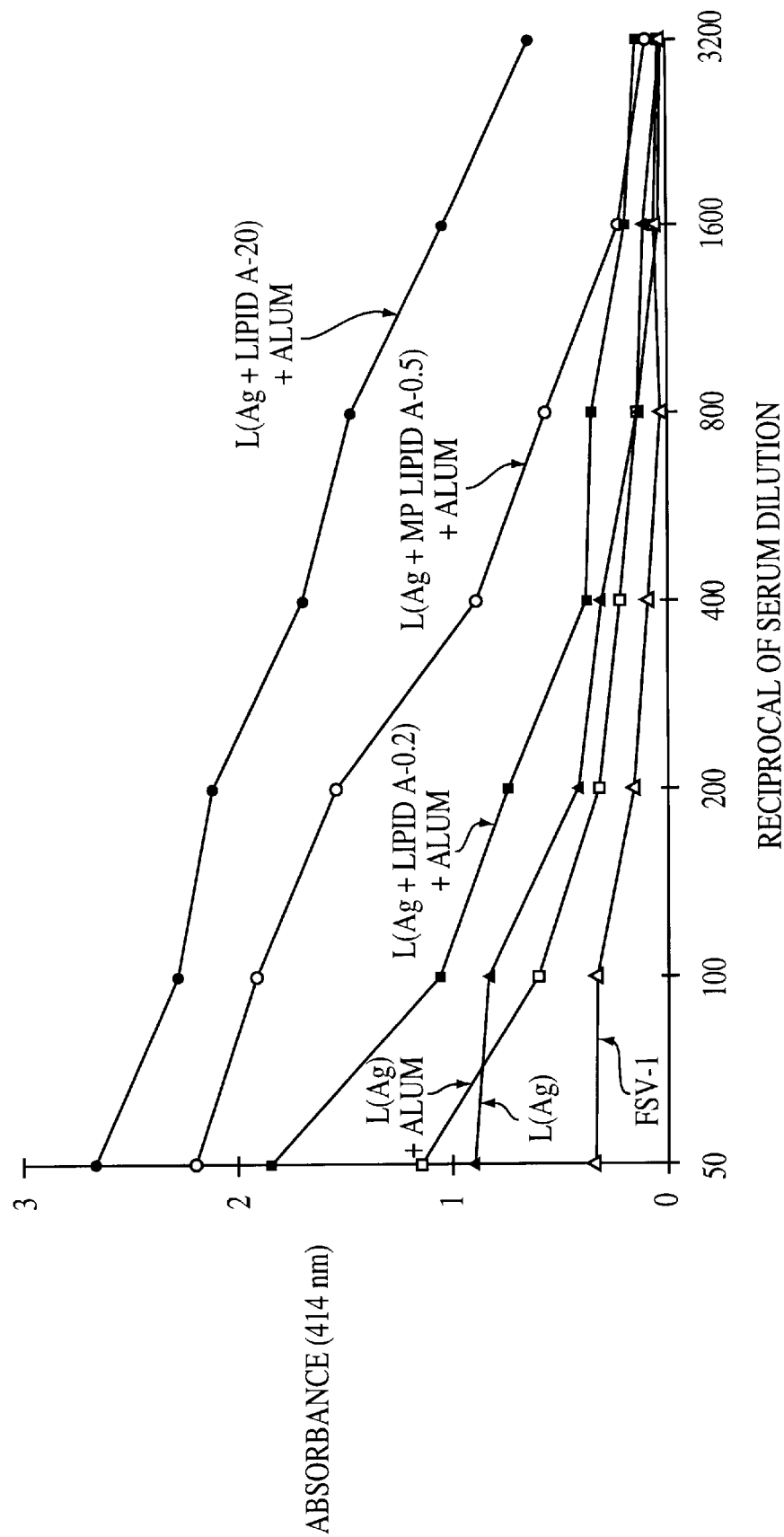

FIG. 5 shows the immune response to liposomal R32tet$_{32}$ in monkeys at 6 weeks after primary immunization.

Figure 6:
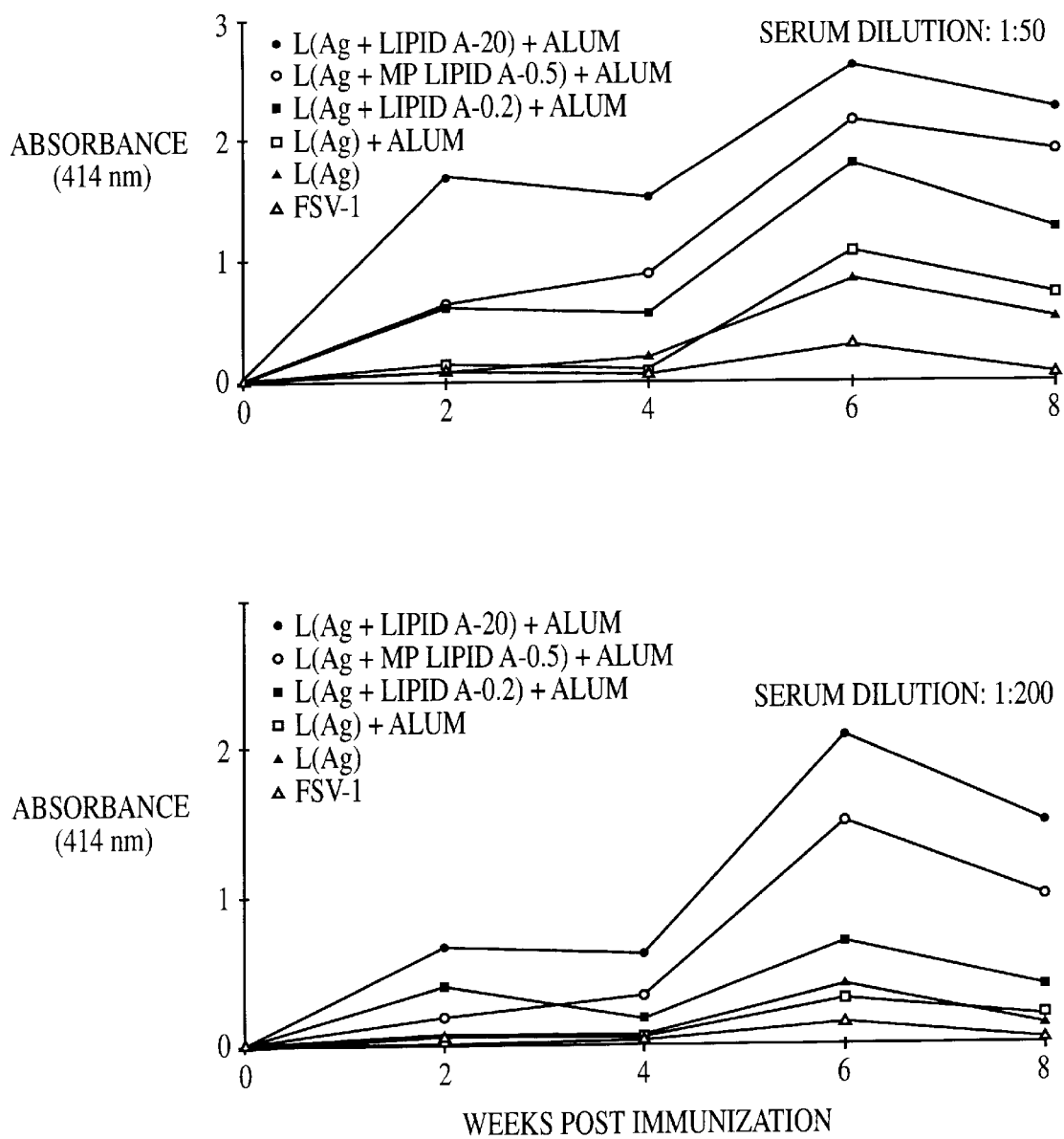

FIG. 6 shows the time course of the immuno response to liposomal vaccines in monkeys.

DETAILED DESCRIPTION OF THE PREFERRED EMBODIMENTS

It has been discovered that an unexpectedly large increase in antibody activity against a malarial antigen occurs in mammals injected with liposomes that comprise the antigen and lipid A and that are adsorbed to aluminum hydroxide. The enhancement in antibody activity can vary, but increases of 800-fold or more have been realized in accordance with the present invention.

In this regard, it is generally expected that a vaccine prepared in accordance with Good Manufacturing Practices ("GMP") prescribed by the U.S. Food and Drug Administration will be less potent than one prepared otherwise. This expectation holds true for the above-described vaccine. Yet, the reduction in potency of the vaccine within the present invention is much less than that of a vaccine that comprises the antigen alone adsorbed to aluminum hydroxide.

The ability, within the present invention, to use a nonpyrogenic fraction of lipid A or a nonpyrogenic amount of lipid A to stimulate an increase in antibody activity could not have been predicted.

It has further been found that Rhesus monkeys can be used as models for human treatment since, like humans, injection of a malarial antigen alone induce only low titers of antibody to the antigen. In contrast, injection of a small amount of a malarial antigen alone into rabbits and mice induces high antibody titers.

Within the present invention, a "malarial antigen" is an antigen that is capable of inducing an immune response against a malarial parasite in humans and/or in animals. Such an antigen can be unconjugated or can be a hapten conjugated to a carrier molecule.

Malarial antigens suitable for use in the context of the present invention include (1) a natural antigen of a malarial parasite or a malarial parasite-infected cell or a portion of such conjugated to a carrier or, (2) a synthetic protein or peptide that has the entire amino acid sequence of a natural malarial antigen or a portion thereof conjugated to a carrier.

Natural malarial antigens can be isolated by harvesting the parasite or parasite-infected cells from mosquitos and/or an infected host, lysing the parasites or cells, then isolating and purifying one or more antigens therefrom. For example, the following antigens are suitable for use in the present invention:

(a) a protein localized on the surface of sporozoites, prepared as described in Nussenzweig et al., *J. Exp. Med.* 156: 20 (1982), the contents of which are incorporated herein by reference;

(b) a 195 KD (kilodaltons) protein on the surface of merozoites or its cleavage products: proteins of 83 KD, 42 KD and 19 KD, prepared as described in Freeman and Holder, *J. Exp. Med.* 158: 1647 (1983), the contents of which are incorporated by reference;

(c) a 155 KD protein on the surface of *P. falciparum*-infected red blood cells, prepared as described in Perlmann et al., *J. Exp. Med.* 159: 1686 (1984), the contents of which are incorporated herein by reference;

(d) a small molecular weight antigen, about 15 KD to 19 KD from asexual blood stages of *P. falciparum*, prepared as described in International Patent No. WO 88/00597, the contents of which are incorporated herein by reference;

(e) a merozoite surface antigen, about 41 KD to 53 KD from asexual blood stages of *P. falciparum*, prepared as described in International Patent No. WO 88/00595.

A synthetic malarial antigen can be synthesized by a peptide synthesizer according to standard procedures if the amino acid sequence of such a protein is known, for example, in accordance to the method of M. B. Merrifield on a Beckman Peptide Synthesizer Model 990B. Since the amino acid sequence of the CS protein of *P. falciparum* has been established [see Dame et al., *Science* 225: 593–599 (1984), the contents of which are incorporated herein by reference], this protein or a portion thereof can be synthesized in this manner according to the known sequence. Suitable malarial antigens synthesized in this manner includes peptides of the formulas tyr-gly-gly-pro-ala-asn-lys-lys-asn-ala-gly-OH, asp-glu-leu-glu-ala-glu-thr-gln-asn-val-tyr-ala-ala-NH$_2$, and tyr-ser-leu-phe-gln-lys-glu-lys-met-val-leu-NH$_2$, prepared as described in U.S. Pat. No. 4,735,799, the contents of which are herein incorporated by reference.

Alternatively, a synthetic malarial antigen can be produced by recombinant techniques as described in "Guide to Molecular Cloning Techniques" in 152 METHODS IN ENZYMOLOGY, pp. 113–129, Berger and Kimmel ed. (Academic Press, Inc. 1987), the contents of which are incorporated herein by reference, and as described in U.S. Pat. No. 4,707,357, the contents of which are corporated herein by reference.

In a preferred embodiment, a malarial antigen is obtained from bacterial or yeast cells, and comprises several repeats of a portion of the amino acid sequence of a surface antigen of a malaria parasite, prepared as described, for example, in Young et al., *Science* 228: 958–962 (1985), the contents of which are hereby incorporated by reference.

In general, a bacterial plasmid comprising the DNA sequence of a gene encoding a malarial antigen (hereafter "malarial-antigen DNA") can be treated with a restriction endonuclease to excise all or a fragment thereof. This malarial-antigen DNA fragment can be then joined by DNA ligase to another endonuclease-treated bacterial plasmid containing the appropriate genes for expression of the antigenic malaria protein or peptide, and an appropriate marker gene.

The marker gene can be any gene that permits selective growth of only those transformed bacteria carrying the desired plasmids. For example, a marker gene can be a gene conferring the ability to utilize a certain element or compound as nutrient or can be a gene conferring antibiotic resistance to the organism, e.g., a tetracycline resistance ("$Tet^r$") gene. Propagation of those bacterial cells that carry the malarial-antigen DNA in their plasmids would yield the desired recombinant molecules that can serve as malarial antigens.

Use of recombinant DNA techniques to produce malarial antigens can result in the production of plasmids of varying lengths, e.g., $pR16tet_{32}$, $pR32tet_{32}$ and $pR48tet_{32}$, that encode the peptides $R16tet_{32}$, $R32tet_{32}$ and $R48tet_{32}$, respectively, the peptides having the definitions given above. Peptides that are smaller in size, e.g., $R16tet_{32}$, can be used as a hapten to produce a malarial antigen after conjugation to larger molecules such as bovine serum albumin or other albumins. Another malarial antigen synthesized by recombinant technique is an antigen designated FSV-2 made in *E. coli* and comprises the amino acid sequence of a portion of the CS protein of *P. falciparum*, as follows:

wherein A denotes alanine, C denotes cysteine, D denotes aspartic acid, E denotes glutamic acid, F denotes phenylalanine, G denotes glycine, H denotes histidine, I denotes isoleucine, K denotes lysine, L denotes leucine, M denotes methionine, N denotes asparagine, P denotes proline, Q denotes glutamine, R denotes arginine, S denotes serine, T denotes threonine, V denotes valine, and W denotes tryptophan. See also International Patent No. WO 87/06939, the contents of which are incorporated herein by reference.

Immunogenic polypeptides comprising the tetrapeptide repeats of the *P. falciparum* circumsporozoite protein include $RNS1_{81}$ polypeptides. $R32NS1_{81}$ has been found to be highly effective for causing immune response in mammals to *P. falciparum* sporozoites. $R32NS1_{81}$ comprises the R32 antigenic sequence fused to 80 N-terminal amino acids of NS1. In the fusion, R32 is fused to the second amino acid of NS1; at the C-terminus, amino acid 81 of NS1 is fused to a sequence of -Leu-Val-Asn. Thus the sequence is:

N-Asp-Pro-(Asn-Ala-Asn-Pro)$_{15}$-(Asn-Val-Asp-Pro)-(Asn-Ala-Asn-Pro)$_{15}$-Asn-Val-$NS1_{81}$-C wherein the term "$NS1_{81}$" used above includes the residues Leu-Val-Asn fused at the C-terminus.

To prepare vaccine within the present invention, liposomes comprising lipid A which have been previously dried, as described in more detail below, are mixed and rehydrated in the presence of a malarial antigen and a medium suitable for injection, e.g., Dulbeccos's phosphate buffered saline lacking $CaCl_2$ and $MgCl_2.6H_2O$ ("DPBS, GIBCO Laboratories, Grand Island, N.Y.). The amount of antigen thereby encapsulated can be determined by Lowry protein assay. The preparation is then diluted to a predetermined concentration in DPBS.

The dose of antigen suitable for injection can be determined via routine experimentation. For example, by injecting various groups with different doses of the alum-adsorbed, liposome/lipid A-encapsulated antigen, and monitoring the immune response of each group to determine what dosage induces the highest anti-malarial antibody titer for the longest period of protection. Preferably, the amount of protein or peptide antigen to be injected is less than about 800 $\mu$g, and more preferably in the range of about 30 to about 100 $\mu$g per dose. The number of doses of vaccines to inject also can be determined by routine experimentation. Typically, the dose can vary depending upon the level of rotection desired. For example, after an initial injection at 0 week and a booster at 4 weeks, further booster doses can be injected at monthly, semi-yearly or yearly intervals.

The malarial antigen prepared above can be first mixed with liposomes comprising lipid A for encapsulation and later mixed with aluminum hydroxide for adsorption, as described in more detail below. The vaccine prepared in this manner can be administered via any generally accepted mode of vaccination. For example, it can be taken orally or injected subcutaneously, intramuscularly, intravenously, intradermally or intraperitoneally.

Exemplary of the commercially-available aluminum hydroxide formations that can be used is Amphojel®, an aluminum hydroxide oral antacid which is suitable for animal use. More preferably, especially for human use, is an aluminum hydroxide absorptive gel (hereafter "Alum"), prepared in accordance with the Good Manufacturing Practices (GMP) prescribed by the U.S. Food and Drug Administration. The aluminum hydroxide to be used for adsorption of liposomes can be diluted in PBS. It is to be noted that, consistent with the general observation that the formulation of materials in accordance with GMP causes marked reduction of potency, the potency of a vaccine of the present invention is found to be reduced when Amphojel® is replaced with alum.

Lipid A is a lipoidal constituent of lipopolysaccharide ("LPS") from Gram-negative bacteria, e.g., *E. coli,* Salmonella and Shigella, and can be prepared in the manner described in Alving et al., 2 LIPOSOME TECHNOLOGY 157–175, G. Gregoriadis, ed. (CRC Press 1984). In essence, LPS is prepared by phenol-extraction or by trichloroacetic acid treatment of such bacterial cells. Lipid A can also be purchased from available commercial sources, e.g., Calbiochem-Behring (La Jolla, Calif.), List Biological Laboratories, Inc. (Campbell, Calif.) and Ribi Immunochem Research, Inc. (Hamilton, Mont.). LPS is similarly available from commercial sources, e.g., Difco (Detroit, Mich.), List Biological Laboratories, Inc. and Ribi Immunochem Research, Inc.

For extraction of lipid A from LPS, the LPS is heated in a boiling water bath for about two hours in about 1% acetic acid in an amount of 10 mg of LPS per ml. The precipitate formed is washed three times with distilled water by centrifugation at 4° C. and then lyophilized. To purify the lipid A so obtained, an aqueous solution of about 0.5% triethylamine ("TEA") is used for solubilization of lipid A in the water phase. This solution is allowed to stand for about 10 to 30 minutes. The phases are separated, with or without centrifugation at about 12,000×g for about 10 minutes. The resulting purified lipid A is chloroform soluble and may be analyzed for phosphate content. In general, about 1 $\mu$g of the chloroform-soluble lipid A from *E. coli,* strain 0111 LPS (from Difco) contains about 0.3 nmol of phosphate, and 1 $\mu$g from Salmonella lipid A contains about 0.7 nmol of phosphate.

Phospholipids are used for preparing the liposomes employed in the context of the present invention. In contrast to other studies, it has been found that liposomes carrying a net positive charge or a net negative charge, or that are neutral, are all effective as adjuvants in the present invention. Accordingly, the liposomes to be used herein can carry a net positive charge, a net negative charge or can be neutral. Dicetyl phosphate can be employed to confer a negative charge on the liposomes, and stearylamine can be used to confer a positive charge on the liposomes. Preferably, the phospholipids to be used are diacylglyerols in which at least one acyl group comprises at least twelve carbon atoms, preferably between about fourteen to about twenty-four carbon atoms. It is also preferred that at least one head group of the phospholipids, i.e., the portion of the molecule containing the phospho-group, is a phosphocholine, a phospho-ethanolamine, a phosphoserine or a phosphoinositol.

Lipids suitable for use in the context of the present invention can be purchased from commercially sources. For example, dimyristoyl phosphatidylcholine ("DMPC") can be purchased from Sigma Chemical Co.; dicetyl phosphate ("DCP") is available from K and K Laboratories (Plainview, N.Y.); cholesterol ("Chol") from Calbiochem-Behring; dimyristoyl phosphatidylglycerol ("DMPG") and other lipids from Avanti Polar Lipids, Inc. (Birmingham, Ala.) Stock solutions of lipids in chloroform or chloroform/methanol can be stored at about −20° C. Preferably, chloroform is used as the only solvent since it is more readily evaporated than methanol.

Phospholipids from natural sources, such as egg or soybean phosphatidylcholine, brain phosphatidic acid, brain or plant phosphatidylinositol, heart cardiolipin, and plant or bacterial phosphatidylethanolamine are preferably not used as the primary phosphatide because of the instability and leakiness of the resulting liposomes.

The liposomes to be used in accordance with the present invention can comprise lipids in any molar ratio and can (but need not) contain cholesterol. Preferably dimyristoyl phosphatidylcholine, dimyristoyl phosphatidylglycerol and cholesterol, respectively, are combined in molar ratios of about 0.9:0.1:0.75, respectively.

Liposomes used herein can be made by different methods. The size of the liposomes varies depending on the method used for making them. A liposome in solution is generally in the shape of a spherical vesicle having one or several concentric layers of lipid molecules each of which is represented by the formula XY wherein X is a lipophobic-hydrophilic moiety and Y is a lipophilic-hydrophobic moiety. In solution, the concentric layers are arranged such that the hydrophilic moiety remains in contact with an aqueous phase. For example, when aqueous phases are present both within and without the liposome, the lipid molecules will, at a minimum, form a bilayer, known as a lamella, of the arrangement XY-YX.

Liposomes within the present invention can be prepared in accordance with known laboratory techniques. In one preferred embodiment, liposomes can be made by mixing together the lipids to be used, including lipid A, in a desired proportion in a container, e.g, a glass pear-shaped flask, having a volume ten times greater than the volume of the anticipated suspension of liposomes. Using a rotary evaporator, the solvent is removed at approximately 40° C. under negative pressure. The vacuum obtained from a filter pump aspirator attached to a water faucet may be used. The solvent normally is removed within about 2 to 5 minutes. The composition can be dried further in a desiccator under vacuum. The dried lipids are generally discarded after about 1 week because of its tendency to deteriorate with time.

The dried lipids can be hydrated at approximately 30 mM phospholipid in sterile, pyrogen-free water by shaking until all the lipid film is off the glass. The aqueous liposomes can be then separated into aliquots, each placed in a vaccine. vial, lyophilized and sealed under vacuum.

In the alternative, liposomes can be prepared in accordance with other known laboratory procedures, e.g., the method of Bangham et al., *J. Mol. Biol.* 13: 238–52 (1965), the contents of which are incorporated herein by reference; the method of Gregoriadis, as described in "Liposomes" in DRUG CARRIERS IN BIOLOGY AND MEDICINE, pp. 287–341 (G. Gregoriadis ed. 1979), the contents of which are incorporated herein by reference; the method of Deamer and Uster as described in "Liposome Preparation: Methods and Mechanisms" in LIPOSOMES (M. Ostro ed. 1983), the contents of which are incorporated by reference; and the reverse-phase evaporation method as described by Szoka, Jr. and Papahadjopoulos, in "Procedure for Preparation of Liposomes with Large Internal Aqueous space and High Capture by Reverse-Phase Evaporation," *Proc. Natl. Acad. Sci. USA* 75: 4194–98 (1978). The aforementioned methods differ in their respective abilities to entrap aqueous material and their respective aqueous space-to-lipid ratios.

The lyophilized liposomes prepared in the above-described manner can be rehydrated and reconstituted in a solution of the malarial antigen and diluted to an appropriate concentration with an suitable solvent, e.g., DPBS. The mixture is then vigorously shaken in a vortex mixer. Unencapsulated antigen can be removed by centrifugation at 29,000×g and the liposomal pellets washed. The washed liposomes can be suspended at an appropriate total phospholipid concentration, e.g., about 20 to about 40 mM. The amount of malarial protein antigen encapsulated can be determined in accordance with the method of Lowry.

After determination of the amount of antigen that is encapsulated in the liposome, the liposomes can be diluted to about 30 μg of antigen per 0.5 ml and can be either bottled immediately or incubated with alum, at approximately 1.0 mg/ml of aluminum, for 1 hr at room temperature, before bottling in vaccine vials, at 3 ml per vial, and storing at 4° C. until use.

For incorporation of lipid A into the liposomes in accordance with the present invention, lipid A can be added to the flask together with the other lipids used for making up the liposomes, i.e., DMPC, Chol, DCP, and all of the lipids can be dried together. In one preferred embodiment, lipid A from *S. minnesota* R595, herein designated "native lipid A," can be included in the liposomes at a concentration of about 0.2 nmoles (hereafter "lipid A-0.2") to about 20 nmoles (hereafter "lipid A-20") of lipid A phosphate per μmol of liposomal phospholipid. In another preferred embodiment, nontoxic monophosphoryl lipid A (hereafter "MP lipid A-0.5") can be used in place of native lipid A at 0.5 nmoles of lipid A phosphate per μmol of liposomal phospholipid. "Monophosphoryl lipid A" as used herein denotes a monophosphoryl fraction isolated from native lipid A that has reduced pyrogenicity when tested in rabbits via established techniques.

Antibody production in response to injection of a vaccine of the present invention can be monitored by enzyme-linked immunosorbent assays (herein "ELISA"), which can be carried out in accordance with established laboratory techniques. In particular, wells of polystyrene microtiter plates can be each coated with 0.1 μg of R32tet$_{32}$ in 0.01 M PBS, pH 7.4. Approximately 18 hr later, the contents of the wells can be aspirated, and the wells filled with blocking buffer, i.e., about 1.0% BSA, 0.5% casein, 0.01% thimerosal and 0.005% phenol red in PBS, and held for 1 hr at room temperature. Sera to be tested, e.g. rabbit sera, can be diluted in blocking buffer, and aliquots of each dilution added to triplicate wells. After a 2-hr incubation at room temperature, the contents of the wells are aspirated, and the wells washed three time with PBS-Tween 20. About 50 μg of horseradish peroxidase conjugated to, e.g., goat-anti-rabbit immunoglobulin G (IgG Bio-Rad Laboratories, Richmond, Calif.) which is diluted 1:500 with 10% heat-inactivated human serum in PBS is then added to each well. After 1 hr, the contents of the wells are aspirated, the wells washed three times with PBS-Tween 20, and 150 μl of peroxidase substrate in buffer is then added to each well. The absorbance at 414 nm can be determined 1 hr later with an ELISA plate-reader device like the TITERTEK MULTISKAN® (Product of Flow Laboratories, Inc., McLean, Va.).

The present invention is further described below by reference to the following examples.

EXAMPLE 1

Clinical use of a malaria sporozoite vaccine, comprising R32tet$_{32}$, for immunization in man and challenge thereof with *P. falciparum*.

Fifteen healthy male volunteers, aged 22–50, who were free from a history of (1) malaria, (2) cardiac, hematological, renal, hepatic or immunological illness, (3) immunosuppressive medication, and (4) preexisting antibodies to blood-stage *P. falciparum* parasites, as determined by immunofluorescent assay, or to R32tet$_{32}$, as determined by an ELISA, were injected with a malarial antigen, R32tet$_{32}$, as described in Ballou et al, *Lancet*, vol. i, pp. 1277–1282 (June, 1987), the contents of which are hereby incorporated by reference. Two such men served as non-immunized controls for the challenge part of the study.

R32tet$_{32}$ is a recombinant molecule comprising a sequence of 32 amino acids identical to that found in a portion of the CS protein of *P. falciparum* and a sequence comprising the first 32 amino acids of a tetracycline resistance gene found in a *E. coli* plasmid. The sequence of R32tet$_{32}$ is identified as follows:

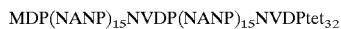

MDP(NANP)$_{15}$NVDP(NANP)$_{15}$NVDPtet$_{32}$ where M=methionine, D=aspartic acid, P=proline, N=asparagine, A=alanine, V=valine, and tet$_{32}$=the first 32 amino acids encoded by the *E. coli* tetracycline resistance gene. The vaccine, designated herein as FSV-1, took the form of single-dose ampules of sterile R32tet$_{32}$ in aqueous saline containing 0.5 mg Al$^{3+}$ (as aluminum hydroxide gel) per 0.5 ml dose. Thiomersal was added as a preservative. FSV-1 was stored at 4° C. and protected from light before administration. The vaccine was prepared at five different concentrations: 10 μg, 30 μg, 100 μg, 300 μg and 800 μg R32tet$_{32}$ per 0.5 ml dose.

The vaccine was given intramuscularly to three volunteers for each of five doses. Volunteer received primary immunization at week 0 and were boosted with identical doses at weeks 4 and 8. Fifty weeks after primary immunization, six of these volunteers received a fourth identical dose. Volunteers were observed for immediate toxic effects for twenty minutes after immunization. Twenty-four and forty-eight hours later, they were examined for evidence of fever, local tenderness, erythema, warmth, induration and lymphadenopathy, and were asked about complaints of headache, fever, chills, malaise, local pain, nausea and joint pain. Before each vaccine dose, blood and urine samples were taken for full laboratory examination. Complete blood count and serum chemistry profiles were rechecked two days after each vaccine dose.

Serum samples were taken from each subject one week after the first dose, then every two weeks for sixteen weeks, and at the time of sporozoite challenge. Previously characterized human sera from malaria-endemic regions of Indonesia and western Kenya were used for comparison. Serum was separated from blood that had clotted overnight at 4° C. and stored at −70° C. until assay.

An ELISA for CS antibodies was carried out in accordance with established laboratory procedures. The test antigen used for the ELISA was R32LR: MDP(NANP)$_{15}$NVDP (NANP)$_{15}$NVDPLR, a purified recombinant construct that contained only the first 2 amino acids encoded by the *E. coli* tetracycline resistance gene. Horseradish peroxidase conjugated to rabbit antihuman-IgG (heavy and light chains) was used to detect antibodies. Assays were run in triplicate and the mean absorbance and standard deviation were calculated for each dilution. Background values at a given dilution were determined with preimmunization samples and defined as an optical density less than the mean plus two standard deviations of the week 0 serum sample's optical density for all volunteers.

Serum samples obtained from the volunteers were assayed for IgG, IgM and IgA antibodies to R32LR by ELISA as described above. IgE antibodies reactive with R32tet$_{32}$ or R32LR were measured by ELISA with biotin-conjugated goat anti-human-IgE as second antibody and detected with streptavidin/horseradish-peroxidase complex. Human IgE myeloma protein was used to prepare a standard curve.

Three weeks after the volunteers had received a fourth dose of FSV-1, six immunized and two non-immunized control volunteers were challenged with the chloroquine-sensitive NF54 strain of *P. falciparum* by allowing 5 mosquitos with a mean salivary gland infection rate of 3.3 to feed. Beginning on day 5 after mosquito feeding, daily thick-blood films were examined for parasites.

The vaccine was found to be well-tolerated at all five doses. There were no episodes of fever, chills, malaise, headache, nausea, or joint pain. Minor pain associated with the injection of vaccine occurred in seven of nine volunteers receiving doses of 100 μg or greater. The injection site was slightly tender in eight of fifteen volunteers after at least one dose of vaccine, including all those receiving 300 μg or 800 μg doses. In no case did these complaints limit function or persist more than 48 hr.

Antigen-specific IgG was detected 2 weeks after the primary immunization and was dose dependent between 100 μg and 800 μg of R32tet$_{32}$. Twelve of fifteen (80%) volunteers had antibody titers of 1:50 or greater. Maximum antibody responses were sustained for 2 to 3 weeks and disappeared with a half-life of about 28 days. The titer rose significantly after repeated doses in only one volunteer, who received the 800 μg dose. His antibody levels were similar to those of the highest-titer sera yet observed from malaria-endemic populations. Immunoglobulin class determinations revealed IgM, IgA, and IgG antibodies to the antigen in all positive serum samples, with IgG antibodies predominating.

About 50 weeks after the first immunization, six volunteers received a fourth dose of FSV-1. Antibody to CS epitopes increased above baseline in four subjects, but all titers were below the maximum titers achieved during the primary immunization. These volunteers and two non-immunized control subjects were challenged by the bite of *P. falciparum*-infected mosquitos 3 weeks after booster dose. Protection appeared to correlate with antibody levels. Parasitaemia was not detected in the volunteer with the highest antibody response and among the subjects who became parasitaemic the incubation and prepatent periods were long in the two subjects with higher antibody titers. The clinical manifestations of malaria were not modified in the two volunteers who had delayed parasitaemia.

EXAMPLE 2

Use of liposomes, lipid A and Amphojel® to enhance the immune response of monkeys to a synthetic malaria sporozoite antigen.

Four Rhesus monkeys per group for a total of 3 groups were each immunized at 0 and 4 weeks with 40-μg doses of (a) R32tet$_{32}$ either as free antigen alone ("Ag"), (b) Amphojel®-adsorbed antigen (hereafter "Ag+Amphojel"), or (c) Amphojel®-adsorbed liposome containing encapsulated antigen and lipid A [hereafter "L(Ag+LA)+Amphojel"].

All injections were done intramuscularly, and each dose was in a volume of 0.5 ml.

The liposomes that were used herein for immunization comprises DMPC, DMPG and Chol, in mole ratios of about 0.9:0.1:0.75. When present, lipid A was included in the liposomes at a concentration of 20 nmol of lipid A phosphate per μmol of phospholipid.

Liposomes were prepared as described above. The lipid mixture in chloroform was dried under vacuum in pear-shaped flasks. After addition of a small quantity of acid-washed 0.5 mm glass beads, the liposomes were swollen in solutions of R32tet$_{32}$ diluted in 0.15M NaCl by 2 min of vigorous shaking in a vortex mixer. Unencapsulated antigen was removed by centrifugation at 12,000 to 15,000×g for 10 min at 20° C., and the liposomal pellets were then washed in 0.15 M NaCl by centrifugation as above. The washed liposomes were suspended in 0.15 M NaCl at a total phospholipid concentration of 20 mM. Liposomes prepared in this manner are adsorbed to Amphojel® as described above.

The antigens to be adsorbed can be mixed with aluminum hydroxide and the mixture can be allowed to stand at 4° C. for about 12 hr. After about 12 hours, sufficient supernatant is discarded so as to yield an aluminum hydroxide concentration of about 0.80 mg to about 1 mg/ml of and an antigen concentration of about 30 μg per 0.5 ml per dose. Results are shown in FIGS. 1 and 2.

Each data point in FIG. 1 represents the mean of all four monkeys in each group. The serum dilution shown is 1:400. This Figure shows that Ag alone was not immunogenic and did not elicit any significant antibody activity. In contrast, about a 2-fold increase in antibody activity was observed at 6 weeks after primary immunization when Ag was combined with Amphojel®, and about a 3-fold increase in antibody activity was observed when Ag was encapsulated in liposomes containing lipid A and adsorbed to Amphojel®. Comparison between the latter two groups shows about a 50% increase in antibody activity in the last-mentioned group.

FIG. 2 shows that all 4 monkeys in the Ag+Amphojel and the [L(Ag+LA)+Amphojel] groups produced high titers of antibodies but none of the monkeys in the Ag group produced antibodies in any significant amounts.

EXAMPLE 3

Use of liposomes, lipid A and aluminum hydroxide, manufactured in accordance with GMP, to enhance the immune response of monkeys to a synthetic malaria sporozoite antigen.

Four monkeys per group were immunized at 0 and 4 weeks with 30 μg of R32tet$_{32}$ which were either (a) adsorbed with alum ("FSV-1"), (b) encapsulated in liposome lacking lipid A ["L(Ag)"], (c) encapsulated in liposomes lacking lipid A and then adsorbed with alum ["L(Ag)+Alum"], (d) encapsulated in liposomes containing a nonpyrogenic dose of native lipid A and then adsorbed with alum ["L(Ag+Lipid A-0.2)+Alum"], (e) encapsulated in liposomes containing a nonpyrogenic dose of monophosphoryl lipid A and then adsorbed with alum ["L(Ag+MP Lipid A-0.5)+Alum"] or (f) encapsulated in liposomes containing a pyrogenic dose of native lipid A and then adsorbed with alum ["L(Ag+Lipid A-20)+Alum"].

The foregoing vaccines were prepared as described above and the results are shown in FIGS. 3–6. Each point represents the average ELISA activity for 4 monkeys after subtraction of prebleed activity.

FIG. 3 shows the antibody activity induced in undiluted sera of monkeys as a function of time after primary immunization. At 6 weeks after primary immunization, L(Ag)+Alum increased antibody response in monkeys by about 2 to 3-fold as compared to monkeys injected with FSV-1. In comparison, L(Ag+Lipid A-20)+Alum increased antibody response by about 100-fold as compared to monkeys injected with FSV-1.

FIG. 4 shows the ELISA activity of individual monkeys 6 weeks after primary immunization, as represented by individual bars, after substraction of prebleed values. This Figure shows that at a serum dilution of 1:400, none of the monkeys injected with FSV-1 exhibited antibodies to R32tet$_{32}$. In contrast, all the monkeys injected with [L(Ag+Lipid A-20)+Alum] were immunized, that is, all had antibody titer showing absorbance at 414 nm of greater than 0.5 ($A_{414}$>0.5). When lipid A-0.2 was used, 2 of the 4 monkeys injected exhibited high antibody titers, i.e. $A_{414}$>0.5. The highest antibody response was observed with monkeys immunized with a vaccine within the present invention.

FIG. 5 shows the immune response of monkeys at 6 weeks after primary immunization. Each data point in FIG. 5 represents the mean values of the 4 monkeys in each group. This Figure shows, e.g., that at a serum dilution of 1:800, when antibody response in monkeys injected with FSV-1 was negligible, monkeys injected with L(Ag+Lipid A-20)+Alum still exhibited a high antibody response. Therefore, the latter vaccine can be said to induce an increase in antibody response of greater than 800-fold.

The increase in antibody response of the L(Ag+Lipid A-20)+Alum vaccine can even be said to be greater than 3200-fold since at 1:3200 dilution, monkeys injected with FSV-1 showed no antibody activity, whereas monkeys injected with L(Ag+Lipid A-20)+Alum still exhibited an antibody activity of >0.5 ELISA units.

FIG. 5 further shows that at 1:800 serum dilution, monkeys injected with L(Ag+MP Lipid A-0.5)+Alum, a vaccine comprising a nonpyrogenic preparation of Lipid A, exhibited an antibody response of >0.5 ELISA unit while monkeys injected. with FSV-1 showed negligible antibody activity. The former vaccine, therefore, is also able to induce approximately a 800-fold increase in antibody activity in monkeys. Similarly, FIG. 5 shows that the vaccine L(Ag+Lipid A-0.2)+Alum, comprising a nonpyrogenic dose of Lipid A was able to induce an approximate 200-fold increase in antibody activity.

FIG. 6 shows the time course of immune response at two serum dilutions, 1:50 and 1:200.

The large increases in antibody response obtained in this study are entirely unexpected especially in view of only about a 50% increase shown in FIG. 1 of Example 2 above, where monkeys were injected with higher amounts of antigen and the vaccines were made not in accordance with GMP. The ability of a nonpyrogenic portion or dose of lipid A to act as adjuvant is also unexpected.

What is claimed is:

1. A protective vaccine comprising a prophylactically effective amount of aluminum hydroxide-adsorbed liposomes and a medium suitable for injection, wherein said liposomes further comprise lipid A and a malarial antigen, wherein said malarial antigen is $R32NS1_{81}$.

2. A vaccine according to claim 1, wherein said lipid A is native lipid A.

3. A vaccine according to claim 1, wherein said lipid A is monophosphoryl lipid A.

4. A vaccine according to claim 1, wherein said lipid A is given in a non-pyrogenic dose.

5. A vaccine according to claim 1, wherein said liposome is positively charged.

6. A vaccine according to claim 1, wherein said liposome is negatively charged.

7. A vaccine according to claim 6, wherein said liposome comprises phosphatidyl glycerol.

8. A vaccine according to claim 1, wherein said liposome comprises phospholipids with at least one head group selected from the group consisting of phosphoglycerol, phosphoethanolamine, phosphoserine, phosphocholine and phosphoinositol.

9. A vaccine according to claim 6, wherein said liposome comprises dicetyl phosphate.

10. A vaccine according to claim 5, wherein said liposome comprises stearylamine.

11. A method of inducing a protective immune response to a malarial parasite, comprising the step of injecting a human or an animal with a vaccine comprising a prophylactically effective amount of aluminum hydroxide-adsorbed liposomes and a medium suitable for injection, wherein said liposomes further comprise lipid A and a malarial antigen, wherein said malarial antigen is $R32NS1_{81}$.

12. A method according to claim 11, wherein said lipid A is native lipid A.

13. A method according to claim 11, wherein said lipid A is monophosphoryl lipid A.

14. A method according to claim 11, wherein said lipid A is given in a non-pyrogenic dose.

15. A method according to claim 11, wherein said liposome is positively charged.

16. A method according to claim 11, wherein said liposome is negatively charged.

17. A method according to claim 16, wherein said liposome comprises phosphatidyl glycerol.

18. A method according to claim 11, wherein said liposome comprises phospholipids with at least one head group selected from the group consisting of phosphoglycerol, phosphocholine, phosphoethanolamine, phosphoserine and phosphoinositol.

19. A method according to claim 16, wherein said liposome is negatively charged and comprises dicetyl phosphate.

20. A method according to claim 18, wherein said liposome is positively charged and comprises stearylamine.

21. The protective vaccine of claim 1, wherein said $R32NS1_1$ has the sequence

MDP(NANP)$_{15}$NVDP(NANP)$_{15}$NVDPNTVSSFQVD-CFLWHVRKRVADQELGD

APFLDRLRRDQKSLRGRGSTLGLDI-ETATRAGKQIVERILKEESDEALKMTMLVN.

22. The method of claim 11, wherein said $R32NS1_{81}$ has the sequence

MDP(NANP)$_{15}$NVDP(NANP)$_{15}$NVDPNTVSSFQVD-CFLWHVRKRVADQELGD

APFLDRLRRDQKSLRGRGSTLGLDI-ETATRAGKQIVERILKEESDEALKMTMLVN.

* * * * *